United States Patent [19]

Spielman

[11] Patent Number: 5,398,697

[45] Date of Patent: Mar. 21, 1995

[54] APPARATUS FOR MONITORING SPINAL MOTION

[76] Inventor: Steven B. Spielman, 10 Fern Way, Madbury, N.H. 03820

[21] Appl. No.: 239,870

[22] Filed: May 10, 1994

[51] Int. Cl.$^6$ ............................................. A61B 5/00
[52] U.S. Cl. ................................. 128/781; 128/782; 33/511
[58] Field of Search .................. 128/774, 781, 782; 33/511, 512, 514.2

[56] References Cited

U.S. PATENT DOCUMENTS

| | | | |
|---|---|---|---|
| 2,532,915 | 12/1950 | Horner | 128/781 |
| 3,608,541 | 9/1971 | Hall | 128/781 |
| 4,493,382 | 1/1985 | Saito | 128/782 |
| 4,665,928 | 5/1987 | Linial et al. | 128/782 |
| 5,022,412 | 6/1991 | Gracovetsky et al. | 128/781 |
| 5,042,505 | 8/1991 | Mayer et al. | 128/781 |
| 5,143,088 | 9/1992 | Marras et al. | 128/781 |

*Primary Examiner*—Sam Rimell
*Attorney, Agent, or Firm*—Charles I. Brodsky

[57] ABSTRACT

The apparatus of the invention monitors spinal motion to detect movements of the lower back in lifting, bending and twisting through the use of a modified "t"-shaped collimated light beam emitted from a unit worn at the base of the spinal column and detected along the column as long as the spinal motion is within prescribed limits of flexion, extension, and left and right lateral movements—and beyond which an audible signal alert is provided as a warning of unsafe spinal movement.

11 Claims, 5 Drawing Sheets

| FIG. 5A | FIG. 5C |
| --- | --- |
| FIG. 5B | |

APPARATUS FOR MONITORING SPINAL MOTION

FIELD OF THE INVENTION

This invention relates to apparatus for the monitoring of spinal motion and, more particularly, for the detection of unsafe spinal movements as an aid to train the user in proper body mechanics.

Background of the Invention

As is well known and understood, the onset of back pain is accepted as one of the most common reasons for surgical procedures in the United States, and one of the most frequent reasons for hospital admission. Recent publications, for example, assert that the problems of back pain cost American society approximately eighty billion dollars annually (Hochschuler, 1993). Another asserts that the number of lower back injuries exceed 400,000 annually, and represent approximately 1.5% of all worker's compensation injuries (Anderrson, 1993).

It will thus be desirable to have some means available to prevent both the initial lower back injury and any tendency for reinjury to occur. As such low-back injury frequently results from the use of improper body mechanics employed in lifting, bending and twisting techniques, it would also be desirable to have available some type of real-time instructional system to indicate the relative positioning of the sacral to the thoracic spinal regions to reduce or eliminate the risk of low back injuries.

Unfortunately, such apparatus does not exist at the present time. One related patent—U.S. Pat. No. 4,493,328 to Saito—shows a means for detecting head movements in patients with spasmodic torticollis using an unmodulated light emitter and a photosensor, which provides an indication when a patient has not kept their head in a central position aligned with the light beam. Even while not being utilized for the limitation of risk of low back injury and its resulting pain, the described apparatus does not allow for desirable movements to be reinforced, and for reducing undesirable motion.

Another patent in this field—U.S. Pat. No. 5,143,088 to Marras—discloses an apparatus for monitoring motion components of the spine. There, an exoskeleton is utilized along with three potentiometers to measure motion in each of three planes, but no feedback is provided to the wearer for instructional purposes in teaching proper body mechanics.

Objects of the Present Invention

It is an object of the present invention, therefore, to provide apparatus for the detection of unsafe spinal movements and to train the wearer in proper body mechanics so as to reduce or eliminate the risk of lower back injury as frequently caused by incorrect lifting, bending and twisting movements.

It is another object of the invention to provide a simple to use, fully self-contained, inexpensive and easily adjustable device that can be worn throughout the day, without limiting movement in any direction.

It is a further object of the present invention to provide such an apparatus which allows for normal flexion/extension and lateral movements within established parameters, and to warn the wearer of movements beyond these parameters as representative of safe tolerance.

It is yet another object of the invention to provide such apparatus in allowing an evaluation to be made as to the total number of times in any given period that the wearer moves outside the prescribed area of sagittal plane, lateral plane and transverse plane movements as a means of biofeedback as to the success in carrying out the complex movements of flexion/extension, left and right lateral movements, and twisting motions.

SUMMARY OF THE INVENTION

As will become clear from the description that follows, the apparatus of the invention is designed and built to serve as both a training device for the development of proper body mechanics, and as a continuous warning device to reduce the risk of injury in industrial and leisure settings. As will be seen, the apparatus of the invention is lightweight, inexpensive to produce, reliable in its operation and infinitely adjustable through user developed templates. As will further be seen, the apparatus is designed to be electrically operable, to be rechargeable, and to perform for up to eight hours and more, on a single charge.

More particularly, and as will be seen from the description that follows, the apparatus of the invention monitors spinal motion to detect movements of the lower back in lifting, bending and twisting through the use of a modified "t"-shaped collimated light beam emitted from a unit worn at the base of the spinal column and detected along the column as long as the spinal motion is within prescribed limits of flexion, extension, and left and right lateral movements—and beyond which an audible signal alert is provided as a warning of unsafe spinal movement. As will be seen, a light-emitting diode and a Fresnel lens, in a preferred embodiment of the invention, produces this collimated beam of light, and are attached to the back of the wearer over the sacral region of the spine. A specially designed template shapes the collimated beam of light, according to the invention, into desired patterns to detect potentially harmful movements of the spine beyond established parameters, while yet providing full freedom of motion and ambulation. To be more specific, and as will be noted, changes in light intensity are detected along the back of the wearer when attached above the sacral region, and through the use of a photodetector after initial alignment of the light-emitting diode, its Fresnel lens, the template, and the photodetector. When the photodetector senses a spinal movement beyond an established parameter—through the interaction of the templates which pass the light beam, a warning signal is provided—in the nature of an audible alert, for example—as a warning to the wearer and so as to provide instructional training that a proper body mechanic is not being followed.

As will also become apparent, this preferred embodiment of the invention also incorporates a manner of varying the sensitivity of the photodetector picking up the directed, light beam—and in a manner as to make the apparatus of the invention lightweight, inexpensive to produce, reliable in its operation. The apparatus of this preferred embodiment will be seen to be electrically operated, by a battery source of energizing potential, and so as to function for up to eight hours and more, on a single charge.

BRIEF DESCRIPTION OF THE DRAWINGS

These and other features of the present invention will be more clearly understood from a consideration of the following description, taken in connection with the accompanying drawing, in which.

DETAILED DESCRIPTION OF THE DRAWINGS

Figure 1:
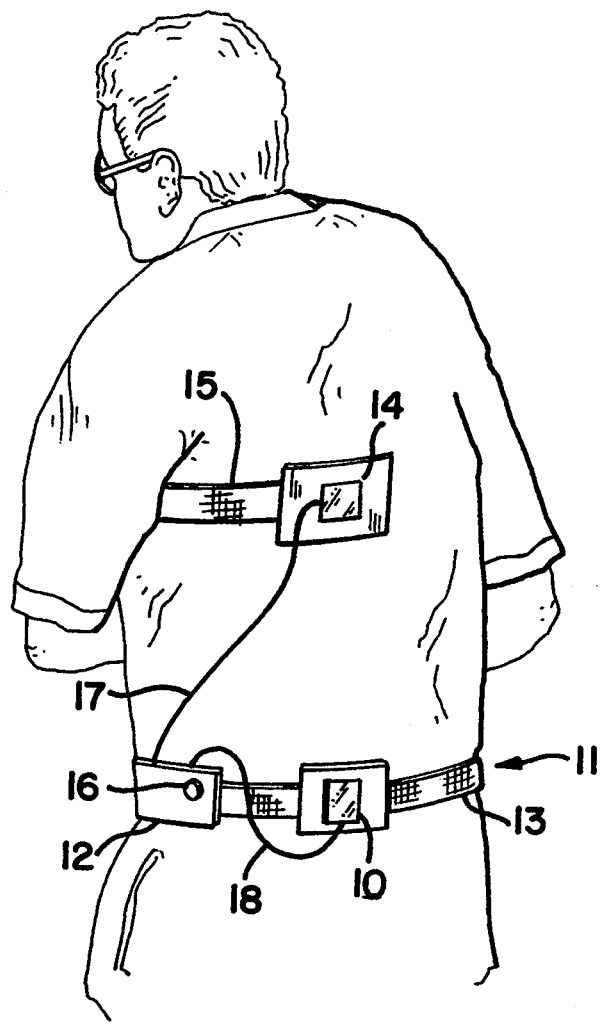
FIG. 1 pictorially illustrates an apparatus for monitoring spinal motion incorporating the features of the invention, as would be worn on the back of an individual to provide spinal positioning feedback and training.

In FIG. 1, a light emitting unit 10, a control box 12, and an elastic strap 13 are fastened tightly to the wearer over the sacral region of the spine (as at 11), fastened tightly to the wearer. A photodetector unit 14 along with an elastic strap 15 are fastened along the spine, and in the vicinity of the thoracic spine. A sensitivity adjustment knob 16 is shown for modulating the intensity of the light emitter, along with appropriate connection wires, 17, 18, as between the control box 12 and the photodetector 14, on the one hand, and between the control box 12 and the light emitter 10, on the other hand.

Figure 2:
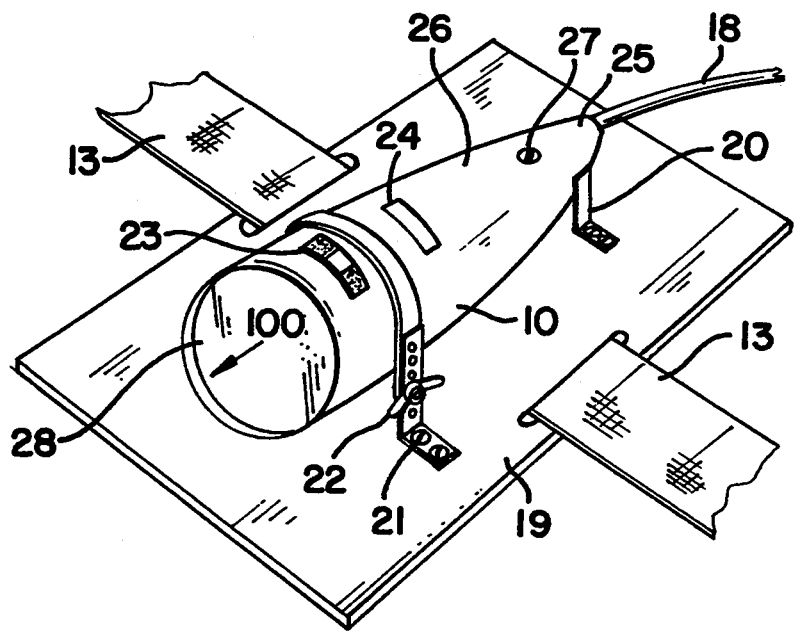
FIG. 2 pictorially shows one manner of attaching the light emitter to the wearer.
Figure 4:
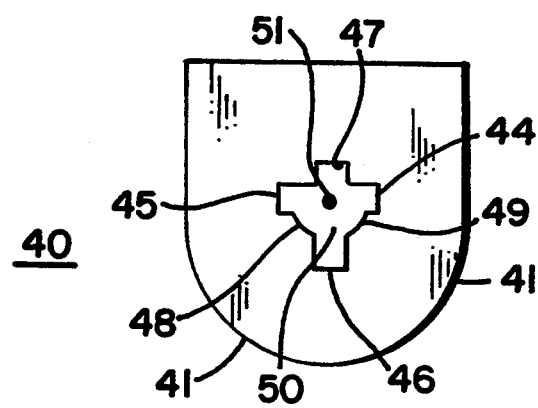
FIG. 4 illustrates a sample template for shaping the collimated light beam into a desired pattern for detecting potentially harmful movements of the spine.

As illustrated in FIG. 2, a light emitter attachment plate 19 is employed, and held tightly to the wearer by means of the elastic strap 13. The light emitter 10 will be seen to be connected to the attachment plate 19 by a fixed bracket 20 and an adjustable bracket 21; as will be appreciated, such brackets 20, 21 allow the light emitter 10 to be adjusted to the individual wearer, for both ease and motion in any direction and worn throughout the day while involved in work or leisure activities—the specific adjustment to the individual wearer being set and locked into position by wing nut 22, for example. A spirit level gauge 23 on the light emitter 10 allows accurate leveling so that the collimated light beam from the emitter 10 projects upwardly, along the spinal column, as at 100. In accordance with the invention, additionally, such light beam is shaped to meet the desired application need through the introduction of a template into a holder 24. That template—an illustration of which is shown in FIG. 4—will thus be inserted between the light source (at 25) in the light source housing unit 26, as secured in place by a retaining screw 27, and a Fresnel lens 28 for providing the collimated light beam at 100. In a preferred embodiment of the invention, a "red" light emitting diode was utilized, along with an elastic neoprene belts 13, 15.

Figure 3:
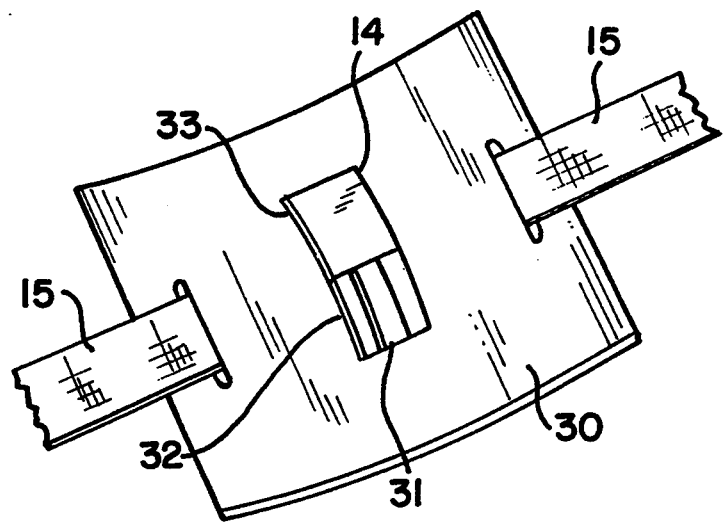
FIG. 3 illustrates a photodetector attachment according to the invention, to be positioned above the sacral region of the spinal column in carrying out the invention.

In FIG. 3, a specially curved photodetector attachment plate 30 is designed to fit into the spinal recess between the longitudinal back extensor muscles at the thoracic spinal region, and with the photodetector unit 14 being placed directly above the curvature. A photodetector limiting template 31 is fixed over the photodetector opening so as to permit certain angles of light to contact the photodetector 14 while blocking other angles. As will be apparent, the photodetector 14 is secured to the attachment plate 30 by brackets 32, 33. In one construction of the invention, such photodetector 14 (and its limiting template 31) can be positioned between 6 and 12 inches from the light emitter 10 in operation, also worn by the wearer through use of an elastic neoprene belt 15, and as a sensititivty adjust in controlling the intensity of the light beam impinging on the photodetector 14.

A sample template according to the invention is shown by the reference numeral 40 in FIG. 4. Such template 40 may be fabricated from a thick black paper in the manner shown, with the outer edges of the template 41 rounded so that the template may fit snugly into the light beam emitting unit of FIG. 2 through the template holder 24.

As FIG. 4 illustrates, the template incorporates a rough, "t"-shaped opening 50, and in one preferred embodiment of the invention was selected to measure 7 mm between its side edges 44, 45, and another 7 mm between its lower and upper edges 46, 47, respectively. Measured with respect to a central point 51, the template design for edge 45 was selected to allow for 10° of lateral movement to the right from this central point 51 (i.e. "neutral") prior to any passing collimated beam; the edge 44, on the other hand, was selected to permit 10° of lateral movement to the left from neutral. At the same time, the lower edge 46 was selected, in this embodiment, to allow 15° of forward flexion to be measured with respect to neutral, while section 47 was selected to allow 5° of extension from neutral prior to triggering a warning stimulus in a manner to be described below. Edge surfaces, 48, 49 which join the edges 45, 46 and 44, 46, respectively are selected to allow for minor rotational movements during situations of limited lateral or forward flexion.

Figures 5, 5A:
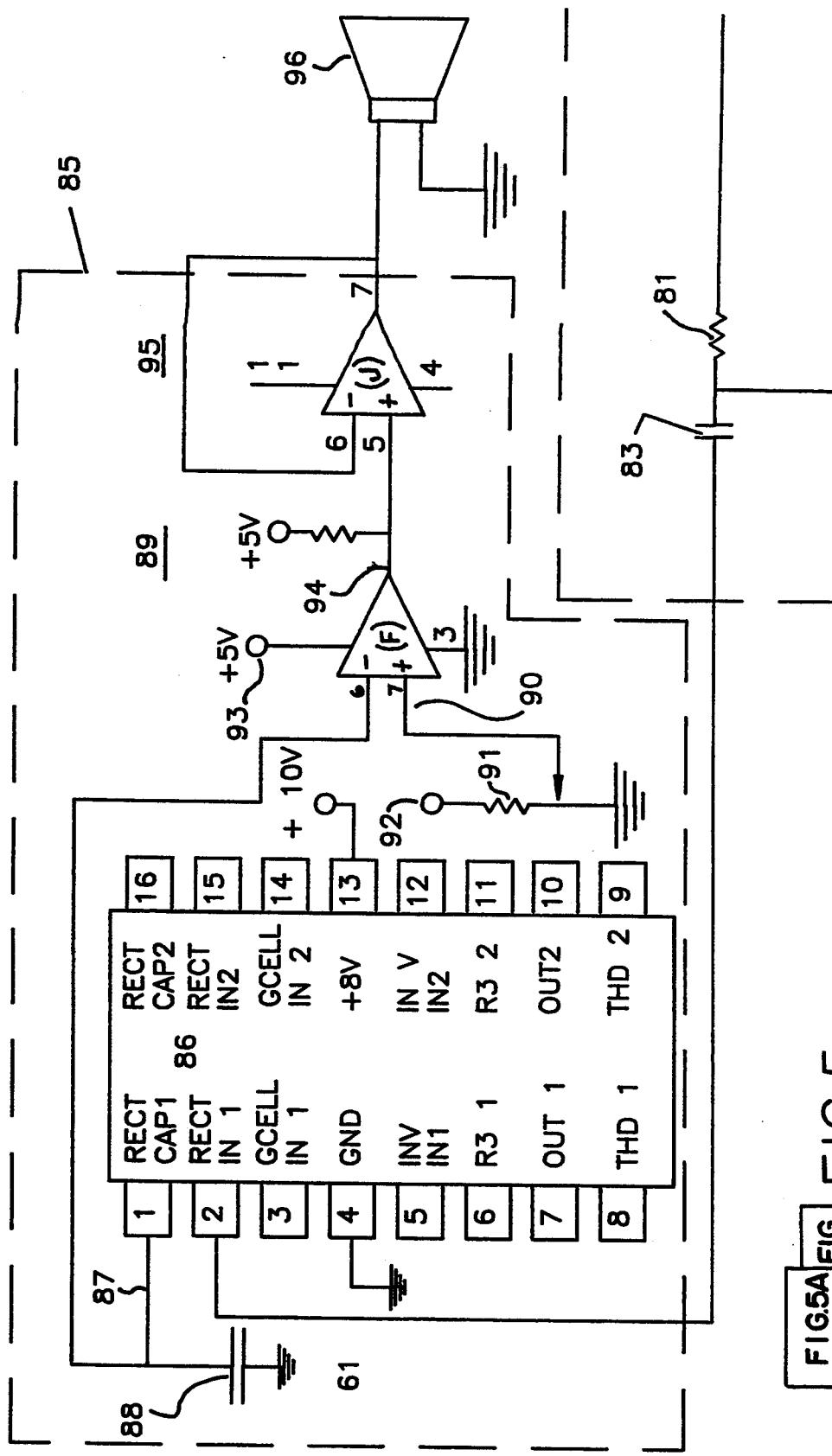
FIG. 5 is an electrical schematic diagram helpful in an understanding of the present invention, and the manner by which an alert signal can be provided to the wearer when spinal movements are detected beyond an established safe parameter consistent with proper body motions within prescribed angles in each of the sagittal, lateral and transverse planes of low back movements.
Figure 5B:
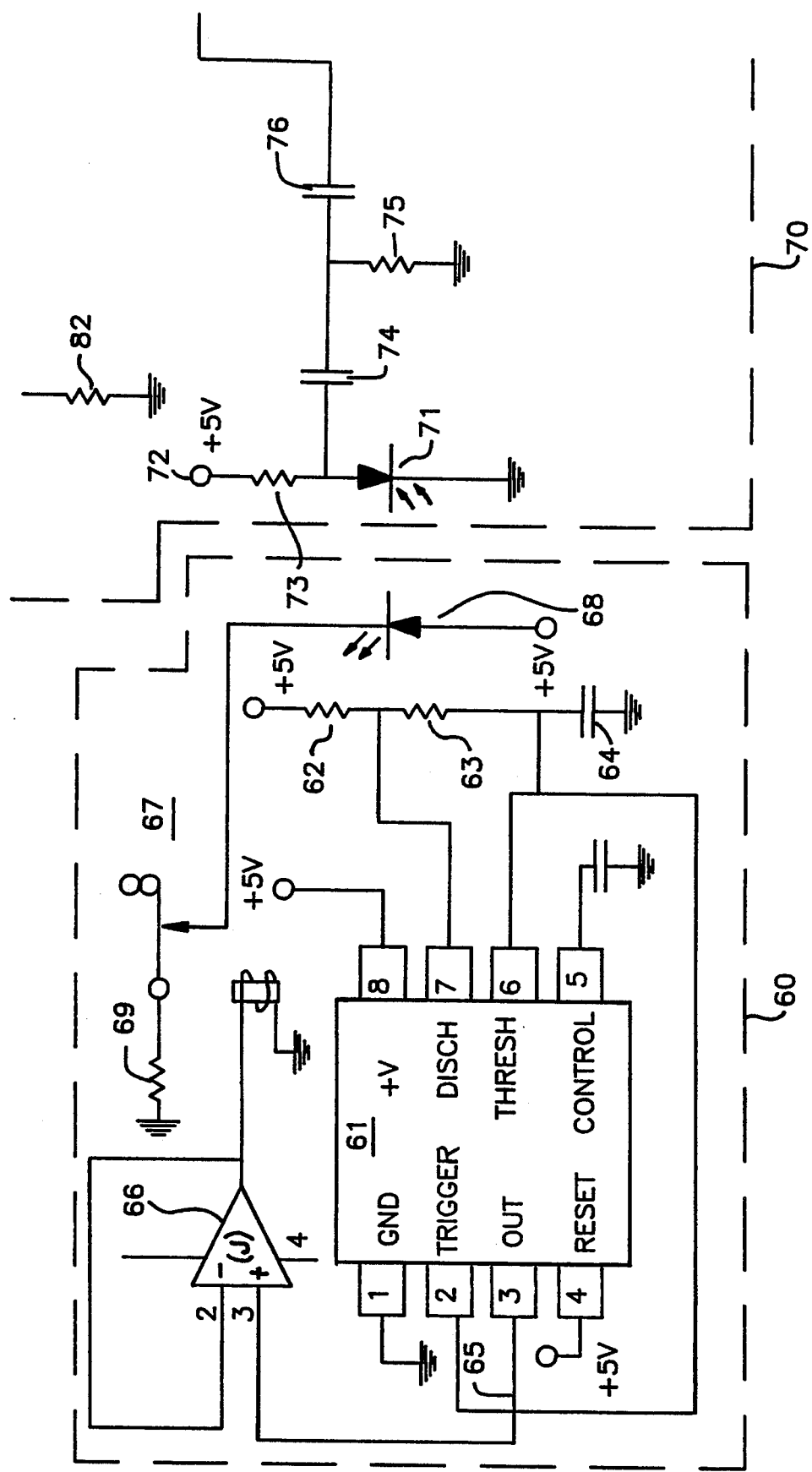
Figure 5C:
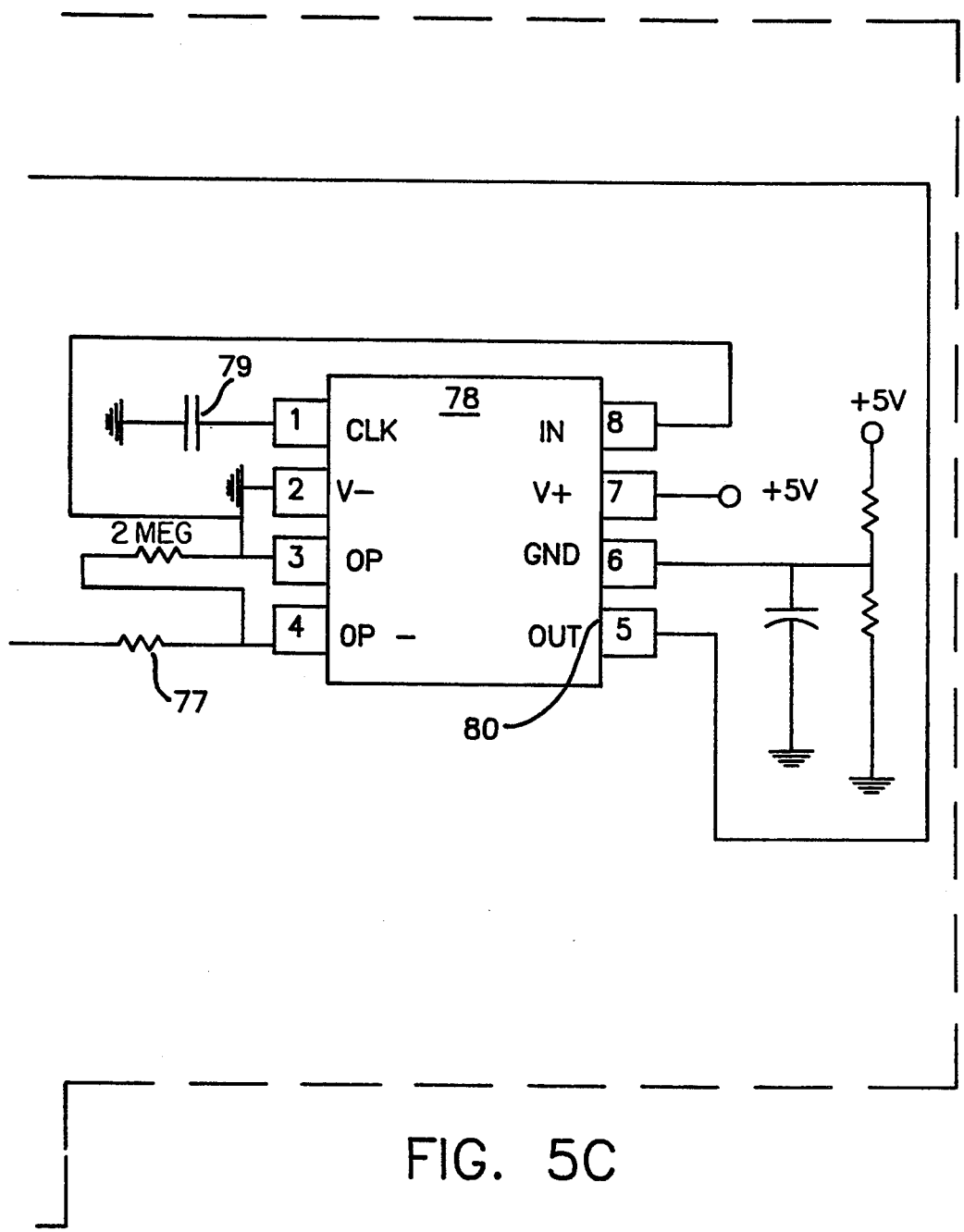

(As will be more readily appreciated from the description of FIG. 5, such "t"-shaped template 40 allows the collimated light beam to pass in reaching the photodetector 14 during such times as the wearer moves prescribed distances in flexion, extension, and left and right lateral movements as determined by the design specifications for the edges 44–49, measured with respect to the central, or neutral point 51. As will be appreciated by those skilled in the art, such templates 40 can be fabricated to meet the needs of a specific training situation, or shaped by a treating professional to define the preferred spinal range of motion for patients with specific movement limitations—beyond which an alarm may be given With the dimensions set forth above, every millimeter increase out from the center of the modified "t"-shape with respect to the neutral point 51 increases the range of motion by approximately 2.9°.)

As previously set forth, with the photodetector 14 aligned with the "cross" of the "t"-shaped light beam passing through the center 50 of the template 40, a wearer of the light emitter and photodetector is able to move prescribed distances in flexion, extension, and left and right lateral movements before any alarm is to be given. Conversely, once such wearer bends or twists to an extent that the photodetector moves outside the prescribed vectors—i.e., the photodetector fails to sense the presence of the emitted collimated light beam—the collimated light beam no longer activates the photodetector 14, and a signal—preferably audible in nature—is provided, so as to allow the wearer to correct the movements in avoiding possible back injury and as a beginning point in developing proper body mechanics in motion. In such manner, programs necessary to support the proper techniques for lifting, bending and twisting can be developed.

Thus, in FIG. 5, the electrical schematic diagram shows the light emitter of the invention by the reference numeral 60, as including an LM 555 timer chip 61 available from the National Semiconductor Company to produce a 5 V square wave at 10 Hz. Resistors 62, 63 and capacitor 64 establish the necessary time constant for such frequency, with the output square wave at its terminal 65 being fed into one terminal of an operational amplifier 66 arranged in a unity gain buffer configuration. The output of the amplifier 66 is then coupled into the controlling coil of a 5 V single pole, single throw relay 67 which serves to activate a light emitting diode 68 in generating a "red" beam of light. As the control signal of relay 67 is a square wave, the light emitting diode 68 turns "on" and "off" at the 10 Hz square wave frequency, with the intensity of the light beam being governed by the value of the resistor 69.

A template, of the type shown in FIG. 4, limits the light output from the diode 68 and produces a rough "t"-shaped beam which is then collimated by the Fresnel lens 28 of FIG. 2. Such collimated "red" beam is then projected along the wearer's spine, to fall on the photodetector 14 (FIG. 3) aligned by its template 31 so that the center of the photodetector 14 aligns with the central point 51 of the "t"-shape. Movements of the wearer's spine within the established parameters designed into the template 40 thus allow the photodetector 14 to continue to receive the light beam emanations from the light emitting diode 68 as collimated by the lens 28. As long as the wearer lifts, bends and twists such that the spinal movements continue to allow the light beam to pass through the template 40 to the photodetector 14, no signal alert is generated However, when the spinal movement results in the absence of the collimated light falling on the photodetector 14, the signal is developed, in the nature of a biofeedback alert to the wearer of an improper body motion to be corrected—whether it results from an improper lifting, improper bending, or improper twisting.

The light detector circuit 70 employs a photocell 71—operative as are all the components of FIG. 5—with a battery source of electrical energizing potential 72, with a resistor 73 in a standard voltage divider circuit. With the photocell 71 operating as a variable resistance whose value depends upon the intensity of the light impinging on it, the voltage developed by the divider increases with increasing light, and vice versa. The capacitor 74-resistor 75 combination acts as a high-pass filter to attenuate any slow changes in light intensity from the signal, as might occur in ambient light. Capacitor 76 and resistor 77 which follow act as a low-pass filter to attenuate any slow changes in light intensity which might occur above 15 HZ, such as ambient 60 Hz fluctuations from household lighting. To further reduce light "noise" above 15 Hz, a switched capacitor low-pass filter 78 of standard construction is employed subsequent to resistor 77. Such a filter circuit is readily available as Max 292 from the Maxim Company, and employs an operational amplifier to increase the magnitude of the incoming signal by the order of 400 times, and with the internal oscillation of the filter 78 being set by capacitor 79 to severely attenuate all signals that may be present above 15 Hz. At the output terminal 80, a pair of resistors 81, 82 and a further capacitor 83 are employed to slightly attenuate the amplified/filtered signal and remove any DC offset that may be introduced by the filter 78. As the light emitting diode transmitter 68 blinks at the square-wave frequency of 10 Hz, the filter circuitry will allow this frequency to pass without any attenuation, but frequencies above 15 Hz and close to DC will be attenuated.

The alarm control circuitry for advising as to proper body mechanics, and to alert as to improper body movements is shown at 85, and includes a full wave rectifier 86 to invert any negative voltages in the incoming signal. When comprised of a Signetics NE 570 integrated chip, the output at the pin 87 couples through a capacitor 88 to smooth the rectified signal into a smooth envelope. A burst of 10 Hz activity thus would produce a smooth 5 V "bump" at 87, indicative of proper body movement. More generally, however, the envelope developed at pin 1 is coupled to the negative input of a National Semiconductor LM 339 comparator 89, whose positive input at 90 is set at 3 V by means of the variable resistor 91 and its own voltage supply at 92. With a 5 V source coupled to terminal 93 of the comparator 89, it will be readily appreciated that its output will be a zero when the envelope voltage is lower than 3 V, and its output will be at 5 V when the envelope is above 3 V. Thus, if a burst of 10 Hz produces rise in the envelope above the 3 V threshold, the comparator output at 94 will change from 5 V to zero volts.

Such signal from comparator 89 is then coupled into a further operational amplifier 95 arranged in a buffer configuration, the output of which is then applied to an operating 5 V buzzer alarm 96. As will be readily appreciated by those skilled in the art, in the absence of the 10 Hz signal in the photodetector output, a 5 V signal is produced by the comparator 94 and the operational amplifier 95, and the alarm 96 sounds to provide an audible alert. On the other hand, if a 10 Hz signal is developed by the photodetector output, the comparator 89 and operational amplifier 95 yields a zero volt output signal, and the alarm 96 is not sounded.

In this operation, therefore, it will be seen that correct body mechanics in flexion, extension, and left and right lateral movements allow the collimated light beam to continue to trigger the photodetector and no audible alert signal results. Once the lifting, bending and twisting motion is improper, so that the photodetector 14 essentially moves outside the prescribed vectors formed by the collimated light beam, no detected signal results, and the audible alert sounds. The wearer will then be able to correct the movements and so potentially avoid back injury, in a program which begins to develop the proper body mechanics to support the proper techniques for lifting, bending and twisting. As will be understood, just at what points and manners of movement the audible alert sounds is established by the particular design of the template utilized in setting the desired spinal range of motion of the wearer, depending upon his or her needs.

While there has been described what is considered to be a preferred embodiment of the present invention, it will be readily appreciated by those skilled in the art that modifications can be made without departing from the scope of the teachings herein. For at least such reason, therefore, resort should be had to the claims appended hereto for a true understanding of the scope of the invention.

I claim:

1. Apparatus for monitoring spinal motion, comprising:

first means, worn by a wearer over the sacral region of the spine, for projecting a collimated beam of light;

second means, worn by a wearer above said sacral region, for detecting said beam of light;

third means, worn between said first and second means, for predeterminedly shaping said beam of light to be detected by said second means;

fourth means for aligning said first, second and third means along the spine in initially detecting said beam of light projected; and fifth means, coupled to said second means, for providing an alert in the absence of any detected light beam.

2. The apparatus of claim 1 wherein said fifth means provides an audible signal.

3. The apparatus of claim 1 wherein said first means includes a light emitting diode and a Fresnel lens.

4. The apparatus of claim 1 wherein said second means also includes means for varying the intensity of said collimated beam of light detected thereby.

5. The apparatus of claim 1 wherein said first and second means are electrically operated by a battery source of energizing potential.

6. The apparatus of claim 1 wherein said third means includes a template to shape said beam of light to a modified "t"-shape when aligned by said fourth means.

7. The apparatus of claim 6 wherein said template shapes said beam of light for detection during prescribed distances in flexion, extension, and left and right lateral movements of the spine.

8. Apparatus for detecting and warning of unsafe spinal movements, comprising:

first means for producing a collimated beam of light;

second means for attaching said first means to the back of the wearer over the sacral region of the spine;

third means for detecting changes in light intensity through the use of a photodetector;

fourth means for attaching said third means to the back of the wearer above said sacral region and providing full freedom of motion and ambulation thereof;

fifth means, including a template, for shaping said light beam into desired patterns to detect potentially harmful movements of the spine;

sixth means for aligning said light beam and said photodetector with the spine; and seventh means for providing a warning signal to alert the wearer when spinal movements are beyond an established safe parameter.

9. The apparatus of claim 8 wherein said fifth means shapes said light beam to detect any one of a potentially harmful lifting, bending, and twisting movement of the spine.

10. The apparatus of claim 8 wherein said fifth means shapes said light beam to detect each one of a potentially harmful lifting, bending, and twisting movement of the spine.

11. The apparatus of claim 8 also including eighth means for controlling the intensity of the beam of light detected by said third means.

* * * * *